(12) United States Patent
El Harouni et al.

(10) Patent No.: US 10,902,588 B2
(45) Date of Patent: Jan. 26, 2021

(54) ANATOMICAL SEGMENTATION IDENTIFYING MODES AND VIEWPOINTS WITH DEEP LEARNING ACROSS MODALITIES

(71) Applicant: International Business Machines Corporation, Armonk, NY (US)

(72) Inventors: Ahmed El Harouni, San Jose, CA (US); Alexandros Karargyris, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 41 days.

(21) Appl. No.: 16/102,212

(22) Filed: Aug. 13, 2018

(65) Prior Publication Data

US 2020/0051238 A1     Feb. 13, 2020

(51) Int. Cl.
*G06T 7/00*     (2017.01)
*G06N 3/08*     (2006.01)
(Continued)

(52) U.S. Cl.
CPC ............ *G06T 7/0012* (2013.01); *G06K 9/628* (2013.01); *G06K 9/6256* (2013.01);
(Continued)

(58) Field of Classification Search
CPC ......... G06T 7/0012; G06T 7/11; G06T 7/143; G06T 2207/20076; G06T 2207/20084;
(Continued)

(56) References Cited

U.S. PATENT DOCUMENTS

| | | |
|---|---|---|
| 9,589,374 B1 | 3/2017 | Gao et al. |
| 10,169,871 B2 | 1/2019 | Hibbard et al. |

(Continued)

FOREIGN PATENT DOCUMENTS

WO     WO2018/015414 A1     1/2018

OTHER PUBLICATIONS

High, Rob, "The Era of Cognitive Systems: An Inside Look at IBM Watson and How it Works", IBM Corporation, Redbooks, Dec. 12, 2012, 16 pages.

(Continued)

*Primary Examiner* — Qian Yang
(74) *Attorney, Agent, or Firm* — Stephen R. Tkacs; Stephen J. Walder, Jr.; William J. Stock

(57) ABSTRACT

A mechanism is provided in a data processing system comprising a processor and a memory, the memory comprising instructions that are executed by the processor to specifically configure the processor to implement a multi-modal classification and segmentation engine for anatomical segmentation identifying modes and viewpoints in biomedical images. The mechanism trains a neural network perform simultaneous classification and segmentation using a set of training images. The neural network provides a classification output that identifies a class label and a second output that identifies a segmentation label. The multi-modal classification and segmentation engine provides a biomedical image as the input image to the neural network. The neural network outputs a plurality of class label probabilities for a plurality of class labels and a plurality of segmentation label probabilities for each of a plurality of segmentation labels. A post-processing component executing within the multi-modal classification and segmentation engine classifies the biomedical image as an identified modality and an identified viewpoint based on the plurality of class label probabilities.

(Continued)

The multi-modal classification and segmentation engine segments the biomedical image based on the plurality of segmentation label probabilities. The multi-modal classification and segmentation engine outputs the classified and segmented biomedical image.

20 Claims, 6 Drawing Sheets

(51) Int. Cl.
    *G16H 30/20*     (2018.01)
    *G06K 9/62*     (2006.01)
    *G06T 7/143*     (2017.01)
    *G16H 30/40*     (2018.01)
    *G06T 7/11*     (2017.01)

(52) U.S. Cl.
    CPC ............. *G06K 9/6277* (2013.01); *G06N 3/08* (2013.01); *G06T 7/11* (2017.01); *G06T 7/143* (2017.01); *G16H 30/20* (2018.01); *G16H 30/40* (2018.01); *G06T 2207/20076* (2013.01); *G06T 2207/20081* (2013.01); *G06T 2207/20084* (2013.01)

(58) Field of Classification Search
    CPC .......... G06T 2207/20081; G06K 9/628; G06K 9/6256; G06K 9/6277; G06N 3/08; G16H 30/20; G16H 30/40
    See application file for complete search history.

(56) References Cited

U.S. PATENT DOCUMENTS

| | | |
|---|---|---|
| 2016/0093048 A1 | 3/2016 | Cheng et al. |
| 2016/0292859 A1* | 10/2016 | Magda ...................... G06T 7/33 |
| 2017/0011185 A1 | 1/2017 | Schweizer |
| 2017/0228896 A1 | 8/2017 | Yu et al. |
| 2019/0005684 A1* | 1/2019 | De Fauw ............. G06K 9/6262 |
| 2019/0156477 A1 | 5/2019 | Perrin et al. |
| 2019/0290228 A1 | 9/2019 | Vija |
| 2019/0362835 A1* | 11/2019 | Sreenivasan .......... G06T 7/0012 |

OTHER PUBLICATIONS

Simonyan, Karen et al., "Very Deep Convolutional Networks for Large-Scale Image Recognition", ICLR 2015 : International Conference on Learning Representations, May 7, 2015-May 9, 2015, San Diego, CA, 14 pages.

Yuan, Michael J., "Watson and healthcare", IBM Corporation, developerWorks, http://www.ibm.com/developerworks/industry/library/ind-watson/, Apr. 12, 2011, pp. 1-14.

Zhou, Zongwei et al., "Fine-Tuning Convolutional Neural Networks for Biomedical Image Analysis Actively and Incrementally", 2017 IEEE Conference on Computer Vision and Pattern Recognition (CVPR), Jul. 21-26, 2017, 12 pages.

* cited by examiner

FIG. 7
| MODALITY | CLASS LABEL | SEGMENTATION LABEL |
|---|---|---|
| X-RAY | CXR | LUNG, HEART |
| MRI | SAX | MYO, LV, RV |
|  | 2CH | MYO, LV |
|  | 4CH | MYO, LV, RV |
| CT | CT | MYO, LV, RV, LA, RA |
| ULTRASOUND | BMOD | MYO, LV, RV, LA, RA |
|  | DOPPLER | DOPPLER WAVEFORM |
FIG. 8
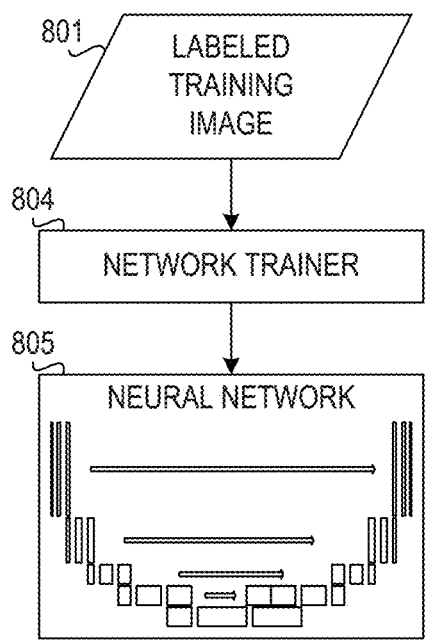
FIG. 9
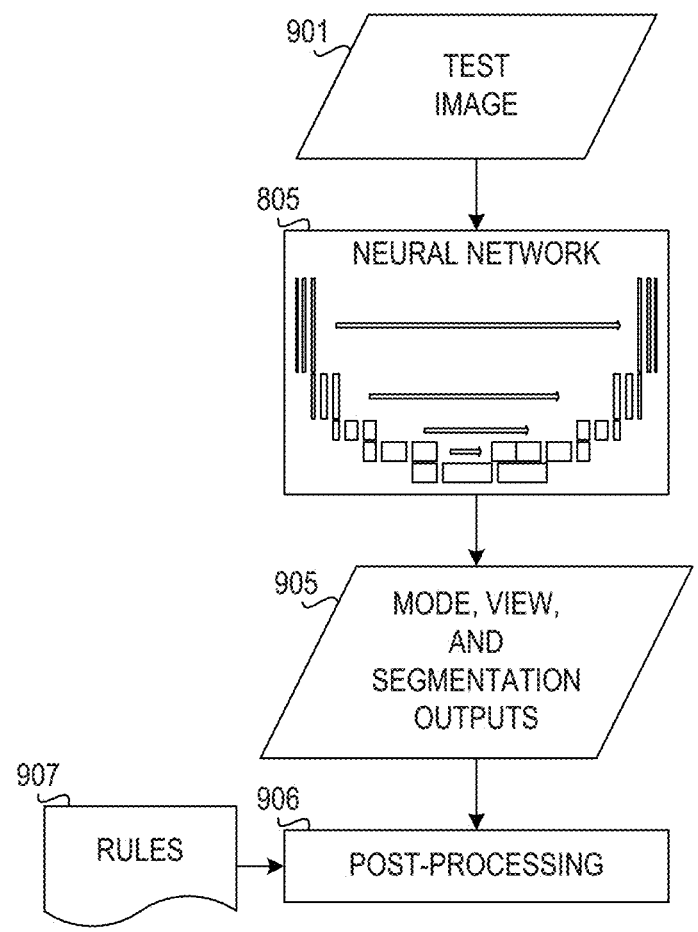

US 10,902,588 B2

ANATOMICAL SEGMENTATION IDENTIFYING MODES AND VIEWPOINTS WITH DEEP LEARNING ACROSS MODALITIES

BACKGROUND

The present application relates generally to an improved data processing apparatus and method and more specifically to mechanisms for training and using a universal multi-modal deep network for classification and segmentation of medical images.

In machine learning, a convolutional neural network (CNN, or ConvNet) is a class of deep, feed-forward artificial neural networks, most commonly applied to analyzing visual imagery. CNNs use a variation of multilayer perceptrons designed to require minimal preprocessing. CNNs are also known as shift invariant or space invariant artificial neural networks (SIANN), based on their shared-weights architecture and translation invariance characteristics. Convolutional networks were inspired by biological processes in that the connectivity pattern between neurons resembles the organization of the animal visual cortex. Individual cortical neurons respond to stimuli only in a restricted region of the visual field known as the receptive field. The receptive fields of different neurons partially overlap such that they cover the entire visual field. CNNs use relatively little pre-processing compared to other image classification algorithms. This means that the network learns the filters that in traditional algorithms were hand-engineered. This independence from prior knowledge and human effort in feature design is a major advantage. They have applications in image and video recognition, recommender systems and natural language processing.

The U-Net is a convolutional neural network that was developed for biomedical image segmentation. The network is based on the fully convolutional network and its architecture was modified and extended to work with fewer training images and to yield more precise segmentations. The network consists of a contracting path and an expansive path, which gives it the u-shaped architecture. The contracting path is a typical convolutional network that consists of repeated application of convolutions, each followed by a rectified linear unit (ReLU) and a max pooling operation. During the contraction, the spatial information is reduced while feature information is increased. The expansive pathway combines the feature and spatial information through a sequence of up-convolutions and concatenations with high-resolution features from the contracting path.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a multi-modal classification and segmentation engine for anatomical segmentation identifying modes and viewpoints in biomedical images, the method comprising. The method further comprises training a neural network perform simultaneous classification and segmentation using a set of training images. The neural network provides a classification output that identifies a class label and a second output that identifies a segmentation label. The method further comprises providing, by the multi-modal classification and segmentation engine, a biomedical image as the input image to the neural network. The method further comprises outputting, by the neural network, a plurality of class label probabilities for a plurality of class labels and a plurality of segmentation label probabilities for each of a plurality of segmentation labels. The method further comprises classifying, by a post-processing component executing within the multi-modal classification and segmentation engine, the biomedical image as an identified modality and an identified viewpoint based on the plurality of class label probabilities. The method further comprises segmenting, by the multi-modal classification and segmentation engine, the biomedical image based on the plurality of segmentation label probabilities. The method further comprises outputting, by the multi-modal classification and segmentation engine, the classified and segmented biomedical image.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 7 is a table that describes the modality/view classifications and segmentation labels identified by the deep learning neural network of the illustrative embodiments;

FIG. 8 is a block diagram of a mechanism for training a neural network to be used for anatomical segmentation and identifying modes and viewpoints in biomedical images in accordance with an illustrative embodiment;

FIG. 9 is a block diagram of a mechanism for using a deep learning neural network to perform anatomical segmentation identifying modes and viewpoints in biomedical images in accordance with an illustrative embodiment;

DETAILED DESCRIPTION

Figure 1:
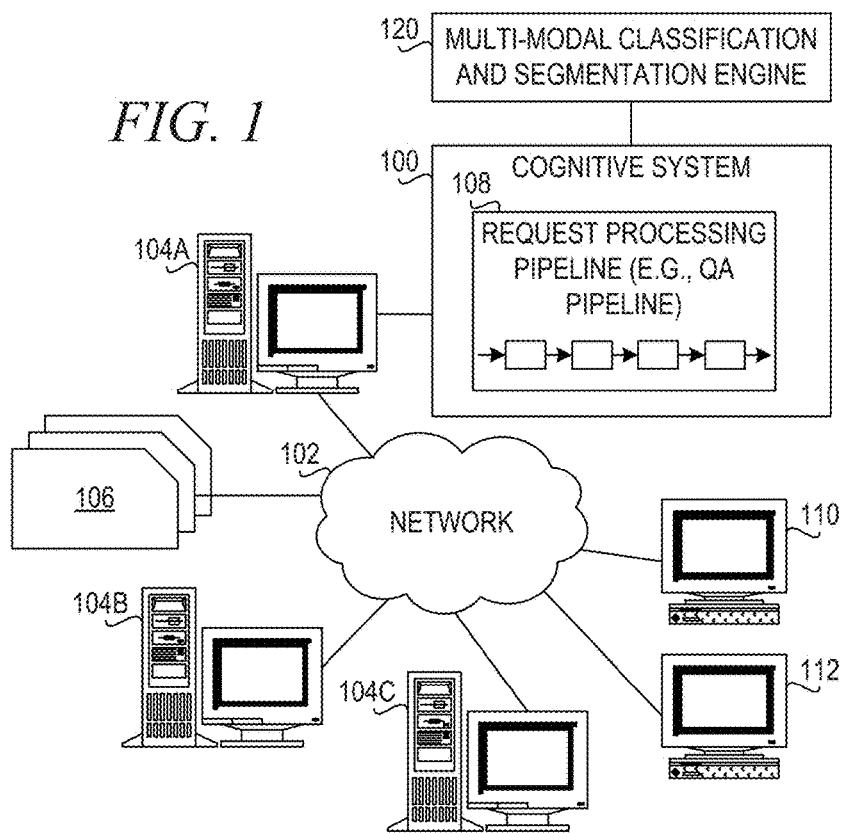
FIG. 1 depicts a schematic diagram of one illustrative embodiment of a cognitive healthcare system in a computer network.

Over the last decade, Deep Learning has become a prominent area of research in machine learning due to recent advances in theory (solvers and optimizers) and infrastructure (larger memory and faster graphic processing units). Convolutional Neural Networks (CNNs) have gained tremendous popularity within the computer vision community because of their ability to automatically capture high level representations of raw images. This approach has elevated the need for hand crafted features customized for each problem. CNNs have shown state-of-the-art results in image classification, object detection, and segmentation. It is because of these reasons that CNNs have taken over the medical image analysis field in the past few years helping achieve great improvements in disease classification, image registration, and anatomy segmentation.

In order to properly train Deep Learning systems, such as CNNs, a large number of examples are required to tune a large number of parameters. In medical image analysis this problem is very critical due to a) the cost of collecting medical images, b) the regulatory constraints of acquiring medical images, and c) the cost and time of annotation (i.e., ground trothing) by clinicians. A previous approach applied by researches was to train a Deep Learning system per medical modality/view to achieve a specific task (e.g., heart ventricle segmentation in MRI). This approach, however, subsequently raises an important technical issue in a radiology setting. It requires a large number of deep learning networks loaded in the memory, each one addressing a specific task. This makes scaling very difficult given the large number of anatomies and modalities found in radiology. Finally, building one network per modality/view per task requires a lot of examples per modality/view, because of the large number of network parameters. However, if the network was decoupled from the modality/view constraint, then examples from various modalities/views could be used together to train this single network. This approach would allow for a more efficient solution because the network could be trained using even a few examples acquired from a new modality/view.

The illustrative embodiment provides a network architecture based on the U-net architecture with two output heads, one for segmentation and the other for classification. The network consists of a concatenating path and an expanding path. The classification output is as the end of the concatenating path, and the segmentation output is at the end of the expanding path. The network is trained both to classify different modalities with different viewpoints (e.g., X-ray, computerized tomography (CT), ultrasound, two-chamber MRI, four-chamber MRI, short axis MRI) and to segment different structures (e.g., lung, heart, Doppler wave form, myocardium (Myo), left ventrical (LV), right ventrical (RV), left atrium (LA), right atrium (RA)).

While the illustrative embodiments may be trained to classify the above-mentioned modalities and viewpoints, other modes and viewpoints may be used to train the network depending upon the implementation and the data available. The modes, viewpoints, and segmentation labels described herein are for illustrative purposes only. The present invention is not to be limited to the examples described herein, although an example embodiment may be specific to a particular set of modalities, viewpoints, or organs/labels for segmentation.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that, the instructions, which execute via the processor of the computer or other programmable data processing apparatus, create means for implementing the functions acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
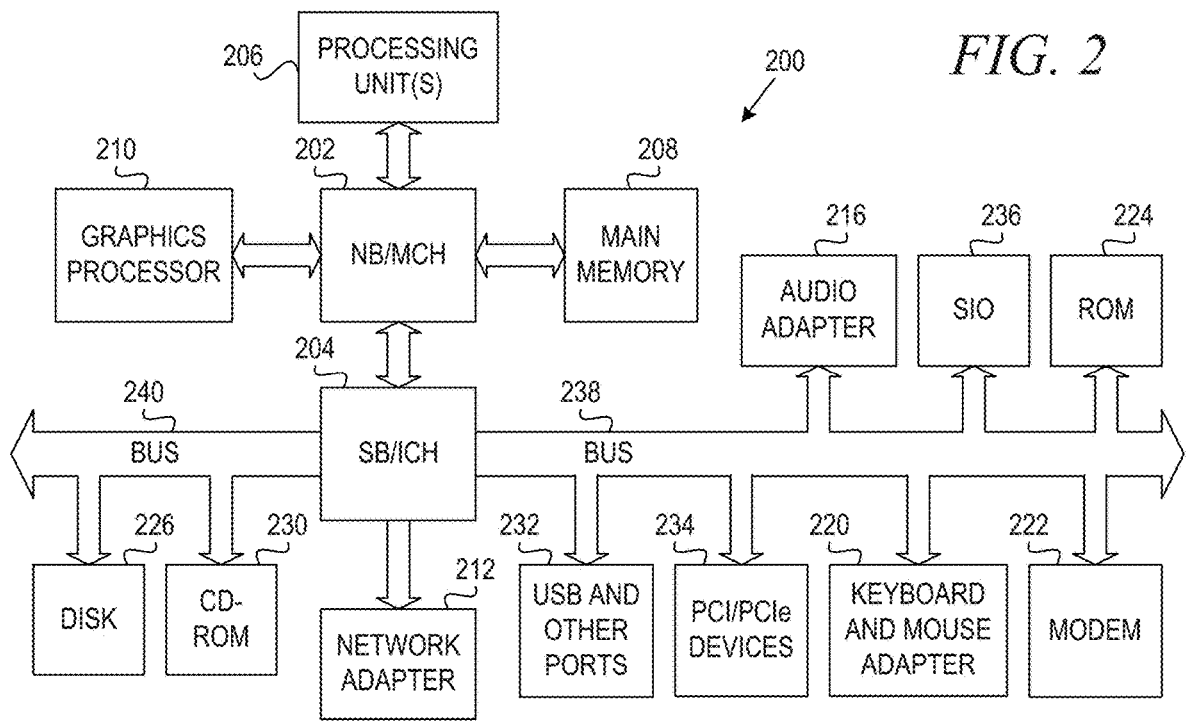
FIG. 2 is a block diagram of an example data processing system in which aspects of the illustrative embodiments are implemented.
Figure 3:
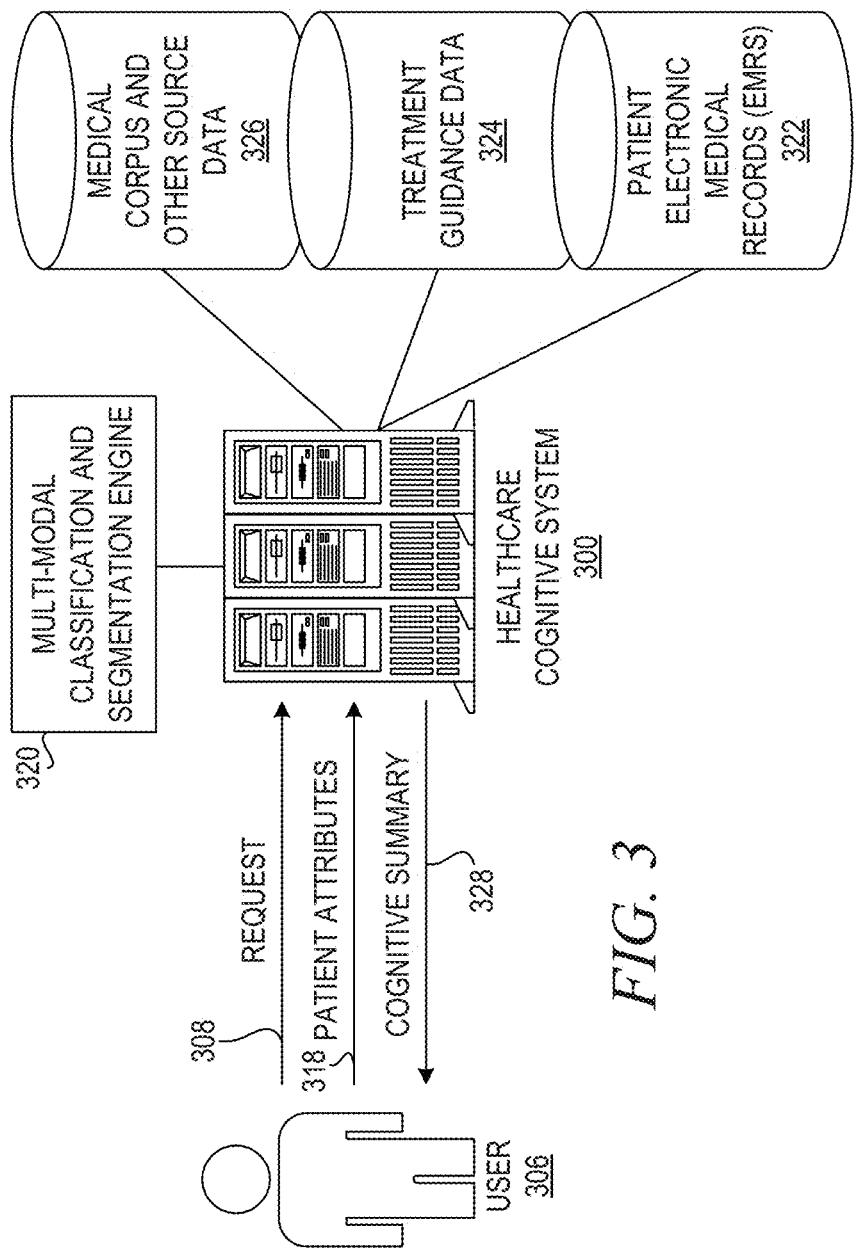
FIG. 3 is an example diagram illustrating an interaction of elements of a healthcare cognitive system in accordance with one illustrative embodiment.

As noted above, the present invention provides mechanisms for detecting anomalies in biomedical images. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have its own associated corpus or corpora that it ingests and operates on, e.g., one corpus for blood disease domain documents and another corpus for cancer diagnostics domain related documents in the above examples. These corpora may include, but are not limited to, EMR data. The cognitive system may use a knockout autoencoder for detecting anomalies in biomedical images.

As will be discussed in greater detail hereafter, the illustrative embodiments may be integrated in, augment, and extend the functionality of these QA pipeline, or request processing pipeline, mechanisms of a healthcare cognitive system with regard to an electronic medical record completeness and data quality assessment mechanism. Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered or processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108, which comprises a plurality of stages for processing an input question/request based on information obtained from the corpus or corpora of data 106, The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process may be repeated for each of the candidate responses to generate a ranked listing of candidate responses, which may then be presented to the user that submitted the input request, e.g., a user of client computing device 110, or from which a final response is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a multi-modal classification and segmentation engine 120 for using a convolutional neural network (CNN) to perform simultaneous modality/view classification and segmentation.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements a cognitive system 100 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. In one embodiment, patient attributes 318 may include identification of a biomedical image for processing for classification and segmentation. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. In one embodiment, patient EMR data 322 includes biomedical images. The cognitive summary 328 is presented in a ranked ordering with associated supporting evidence, obtained from the patient attributes 318 and data sources 322-326, indicating the reasoning as to why portions of EMR data 322 are being provided. Cognitive summary 328 also includes output of classification and segmentation of a biomedical image.

In accordance with the illustrative embodiments herein, the healthcare cognitive system 300 is augmented to include a multi-modal classification and segmentation engine 320 for using a convolutional neural network (CNN) to perform simultaneous modality/view classification and segmentation.

Figure 4:
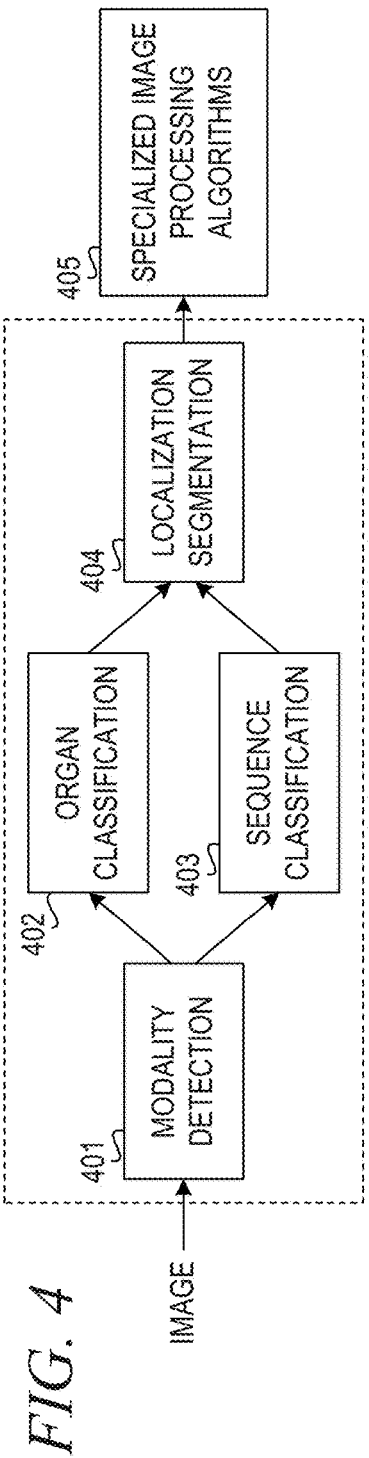
FIG. 4 is a block diagram illustrating a traditional approach using multiple neural networks and different specialized image processing algorithms.

FIG. 4 is a block diagram illustrating a traditional approach using multiple neural networks and different specialized image processing algorithms. An image is provided to modality detection component 401, which detects the modality of the image. Modality detection or classification 401 classifies images into different modalities, such as MRI, CT, ultrasound, X-ray, electrocardiogram (ECG), electroencephalogram (EEG). Organ classification component 402 executes a different neural network or image processing algorithm based on output of modality detection component 401.

Similarly, sequence classification component 403 executes a different neural network or image processing algorithm based on output of modality detection component 401. For example, sequence classification component 403 can classify an MRI image according to sequence type, such as steady-state free precession (SSFP), T1-weighted (T1W), T2W, fluid-attenuated inversion recovery (FLAIR), inversion recovery, etc. Local segmentation component 404 executes one or more neural networks or image processing algorithms based on outputs of organ classification component 402 and sequence classification component 403. Finally, specialized image processing algorithms 405 execute various neural networks or image processing algorithms based on the detected modality, classifications, and segmentations.

Medical image processing algorithms have traditionally focused on a specific problem or disease per modality. Building a system with multiple neural networks and different specialized image processing algorithms is a challenge as each network requires a lot of memory and is computationally heavy. One major disadvantage of such a system is that errors propagate from one level to the next level deteriorating the overall accuracy of the system.

Figure 5:
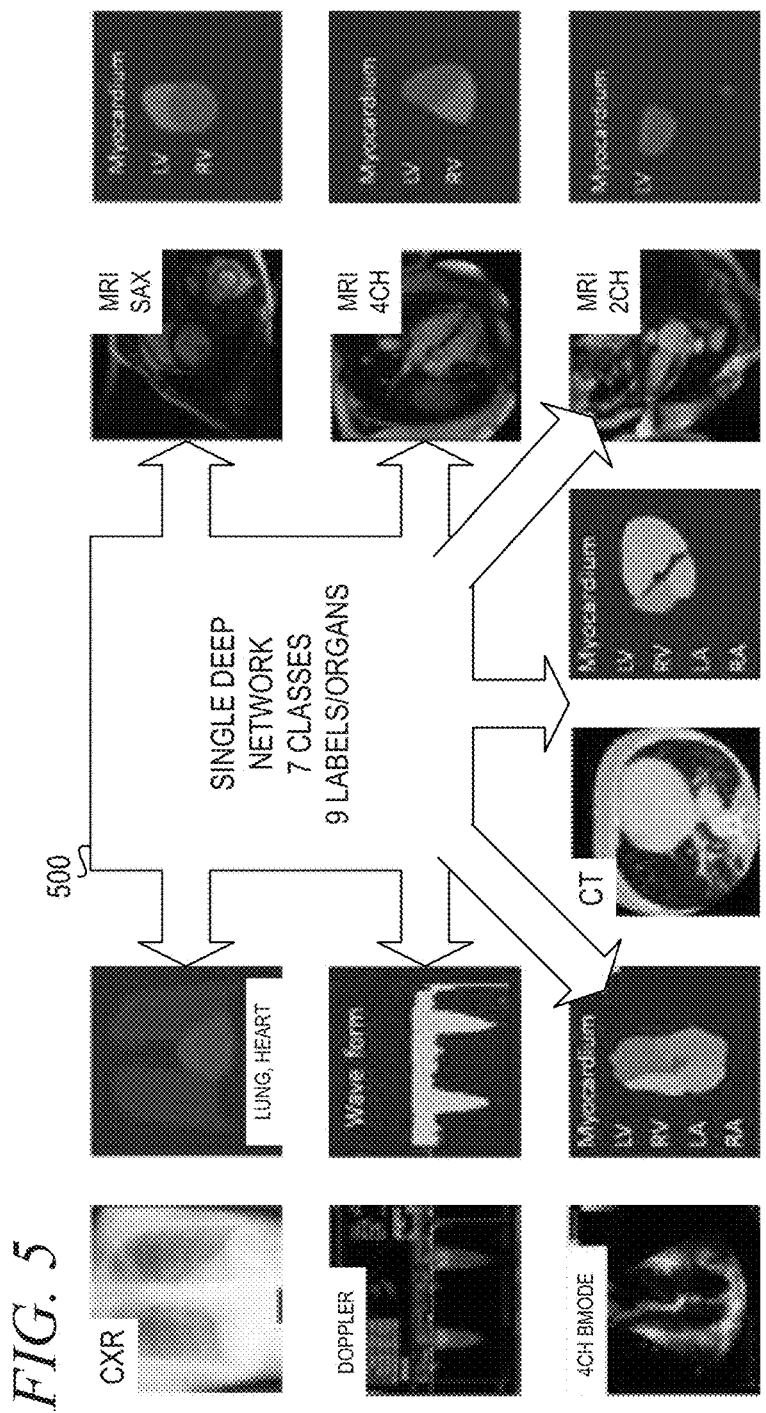
FIG. 5 depicts a network to classify different modalities with different viewpoints and to segment different structures in accordance with an illustrative embodiment.

FIG. 5 depicts a network to classify different modalities with different viewpoints and to segment different structures in accordance with an illustrative embodiment. The mechanisms of the illustrative embodiment combine data from different modalities and viewpoints to train a single deep learning network 500 and train the single universal network 500 for segmentation and classification tasks. The network 500 classifies different modalities with different viewpoints and segments different structures in the input image. The classifier of network 500 determines is computerized tomography (CT), magnetic resonance imaging (MRI), chest X-ray (CXR), ultrasound (US), etc. The viewpoint classifier of network 500 determines the orientation as coronal, sagittal, axial, two-channel view, etc. The organ detection component of network 500 detects particular anatomical structures, e.g., lungs, myocardium, liver, etc. The segmentation segments the anatomical structures of interest with any anomalies, such as tumors, masses, etc.

Figure 6:
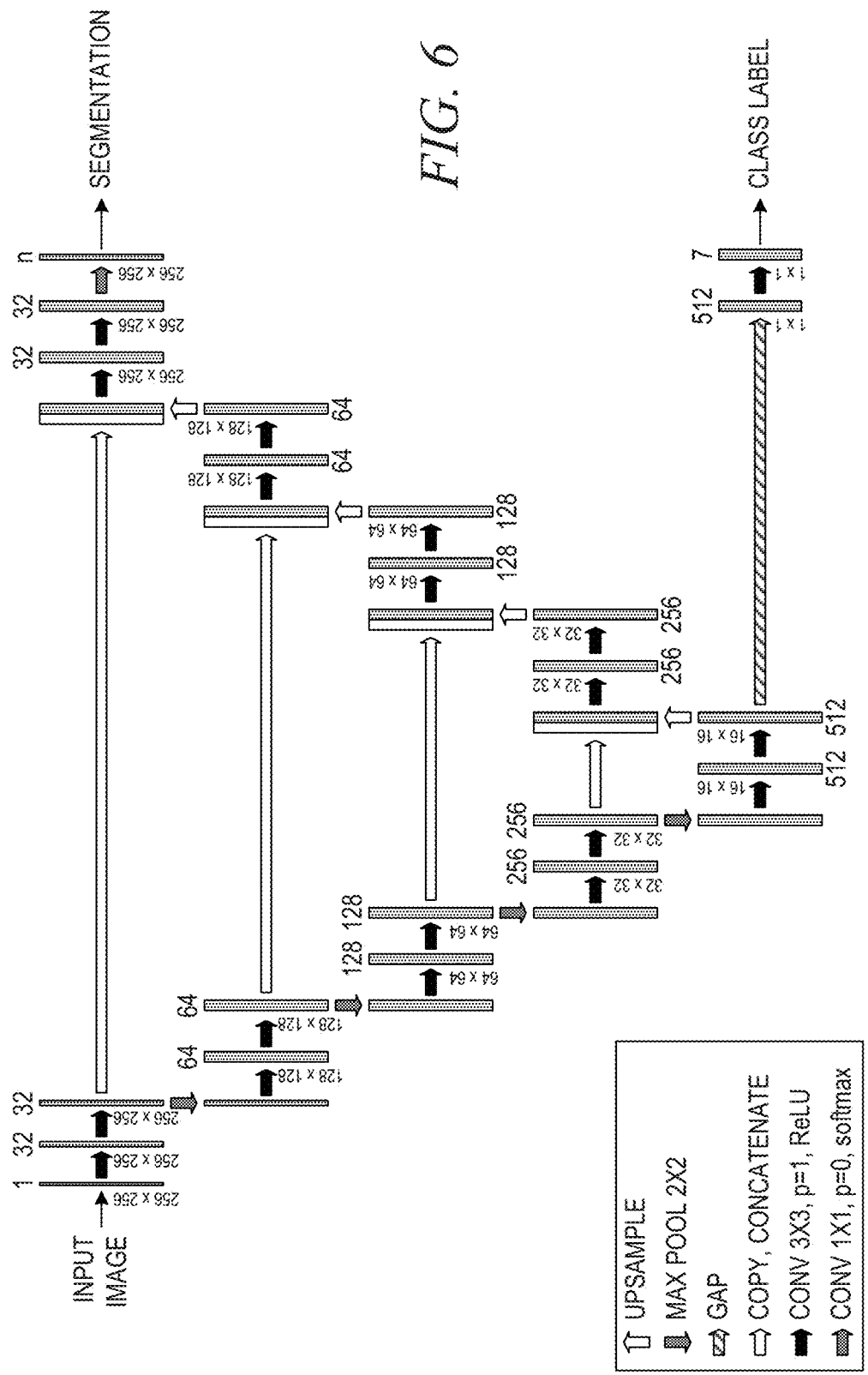
FIG. 6 depicts a U-net for anatomical segmentation identifying modes and viewpoints with deep learning across modalities in accordance with an illustrative embodiment.

The combination of these elements into a single network is achieved by having a two-headed network with two loss functions, one for segmentation and one for classification. FIG. 6 depicts a U-net for anatomical segmentation identifying modes and viewpoints with deep learning across modalities in accordance with an illustrative embodiment. The network architecture is based on the U-net architecture with two output heads, one for segmentation and the other for classification. The network consists of a concatenating path and an expanding path, the classification and segmentation outputs are at the end of the concatenating and expanding paths, respectively. The concatenating path is four levels deep with 2×2 pooling between levels, while the expanding path is connected by an up-sampling filter with 2×2 kernel. All convolutions have a kernel size of 3×3, stried=1, pad=1, followed by a rectified linear unit (ReLU). Padding maintains the size fixed before and after convolution. Each level is composed of two convolutions back to back. The last layer of the segmentation path is n filters (n=the number of segmented structures) of 1×1 convolution followed by a softmax, which gives the probabilities of the segmentation labels. Skip connections between the layers are used to avoid vanishing gradient problem.

For the classification task, the network includes an added global average pooling (GAP) layer at the end of the concatenating path, followed by a convolution layer with seven filters corresponding to the seven classes and finally a softmax layer to produce the class probabilities.

The U-net architecture shown in FIG. 6 is an example CNN that is known for biomedical image segmentation; however, the illustrative embodiments modify and repurpose the U-net architecture to train the U-net as a modality classifier, a viewpoint classifier, an organ detector, and a segmentation mechanism into one network that provides both segmentation and classification. FIG. 7 is a table that describes the modality/view classifications and segmentation labels identified by the deep learning neural network of the illustrative embodiments. The classifier determines if the image is of modality X-ray with class label chest X-ray (CXR); MRI with class labels short axis (SAX), two channel (2Ch), four channel (4Ch); computerized tomography with class label CT; or ultrasound (US) with class labels brightness modulation (Bmod), Doppler (Dop).

For class label CXR, the segmentation mechanism may identify segmentation labels lung, heart. For class label SAX, the segmentation mechanism may identify segmentation labels Myocardium (Myo), left ventrical (LV), right ventrical (RV). For class label 2Ch, the segmentation mechanism may identify segmentation labels Myo, LV. For class label 4Ch, the segmentation may identify segmentation labels Myo, LV, RV. For class label CT, the segmentation mechanism may identify segmentation labels Myo, LV, RV, left atrium (LA), right atrium (RA). For class label Bmod, the segmentation mechanism may identify labels segmentation Myo, LV, RV, LA, RA. For class label Dop, the segmentation mechanism may identify Doppler waveform.

The segmentation head of the U-net generates an image map for each segmentation label. The image map includes a probability for each pixel representing a probability that the pixel is part of that segmentation label. For example, the segmentation head generates an image map for left ventrical, wherein the image map includes for each pixel a probability that the pixel is part of the left ventrical.

FIG. 8 is a block diagram of a mechanism for training a neural network to be used for anatomical segmentation and identifying modes and viewpoints in biomedical images in accordance with an illustrative embodiment. Labeled training image 801 is labeled with the known mode and viewpoint of the image, as well as the known segmentation labels. Training image 801 is provided to network trainer component 802, which then trains neural network 805 to perform anatomical segmentation identifying modes and viewpoints in labeled training image 801.

The process of training neural network 805 is repeated for a plurality of training images, which are selected from multi-modal cardiac images that include MRI, CT, chest X-ray (CXR), and ultrasound. Training images 801 are biomedical images covering all modalities, viewpoints, and segmentation labels. In one embodiment, neural network 805 is a convolutional neural network, and in one example embodiment, neural network 805 is a U-net, which is known to be used for segmentation, but is repurposed and trained for simultaneous multi-modal classification and segmentation.

The deep learning neural network 805 is multi-modal; therefore, it is trained using all modes, e.g., X-ray, MRI, CT, ultrasound. While the prior art may train a mode classifier using all modes, the specialized classifiers and segmentation mechanism would not be multi-modal. That is, a neural network trained for MRI viewpoint classification would be trained only with MRI images. Another neural network might be trained only for segmenting particular organs given one mode or viewpoint. In contradistinction, the neural network 805 is trained to perform segmentation of the left ventrical, for example, regardless of whether the input image is a two-channel Mill image, a CT image, or an ultrasound image.

FIG. 9 is a block diagram of a mechanism for using a deep learning neural network to perform anatomical segmentation identifying modes and viewpoints in biomedical images in accordance with an illustrative embodiment. A test image 901 is an image used to test the deep learning neural network or an image for which a user wishes to perform anatomical segmentation and classification. Test image 901 is provided as input to neural network 805, which generates a probability for each class label and a probability for each segmentation label. Each probability represents a prediction of whether test image 901 matches the corresponding class label or segmentation label. The probabilities make up mode, view, and segmentation outputs 905. The mechanism of the illustrative embodiment then presents the mode, view, and segmentation outputs 905 to the user.

The outputs 905 will include a ranked list of modalities, viewpoints, and segmentations with corresponding percentages. For example, the outputs 905 will include a highest ranked modality (MRI), a highest ranked class label (SAX), and a highest ranked segmentation label (Myo). In most cases, the highest ranked modality, view or class label, and segmentation label will align. It is highly unlikely that the highest ranked segmentation label or class label will disagree with the modality. For example, it is unlikely that the network will produce a high probability for Doppler and Doppler waveform with a modality of X-ray. However, post-processing and specialized image processing algorithms may determine the appropriate combination of modality, viewpoint, and segmentation labels) based on output 905. In the depicted example, post-processing component performs post-processing on outputs 905 and determines a combination of modality, viewpoint, and segmentation label(s) by applying a set of rules 907 to outputs 905.

The segmentations outputs include an image map for each organ/structure, wherein the image map includes a probability for each pixel representing a probability that the pixel is part of the organ/structure. Structures with the highest probabilities are considered the resulted segmentation. Rules of 907 can set a minimum threshold for removing areas of uncertainty (areas with probabilities <0.5). Post-processing 906 applies the threshold to the image maps to determine the pixels that make up the segmentation for a given organ/structure. Moreover, in one embodiment, rules 907 flag images where the relative location of the structures contradict the human anatomy (RA cannot be next to the LV). Also the modality and view point results can help clean up the segmentation be removing small segmentation labels that doesn't belong to this view point.

Figure 10:
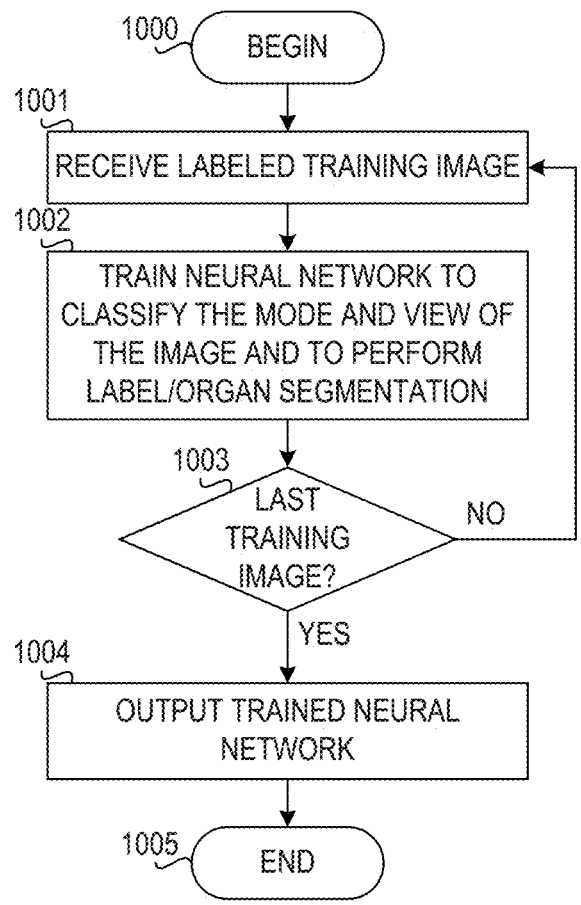
FIG. 10 is a flowchart illustrating operation of a mechanism for training a neural network to be used for anatomical segmentation and identifying modes and viewpoints in biomedical images in accordance with an illustrative embodiment.

FIG. 10 is a flowchart illustrating operation of a mechanism for training a neural network to be used for anatomical segmentation and identifying modes and viewpoints in biomedical images in accordance with an illustrative embodiment. Operation begins (block 1000), and the mechanism receives a labeled training image (block 1001). The mechanism trains the neural network to classify the mode and view of the image and to perform label/organ segmentation (block 1002).

The mechanism determines whether the image is the last training image (block 1003). If the current image is not the last training image, then operation returns to block 1001 to receive the next, training image. If the current image is the last training image at block 1004, then the mechanism outputs the trained neural network (block 1004). Thereafter, operation ends (block 1005).

The network is trained in small batches of images (8-32) at a time. A batch is called one complete epoch. Training is completed for 30-300 epochs depending on data size. The mechanism also decreases the learning rate of the CNN from one epoch to the other.

Figure 11:
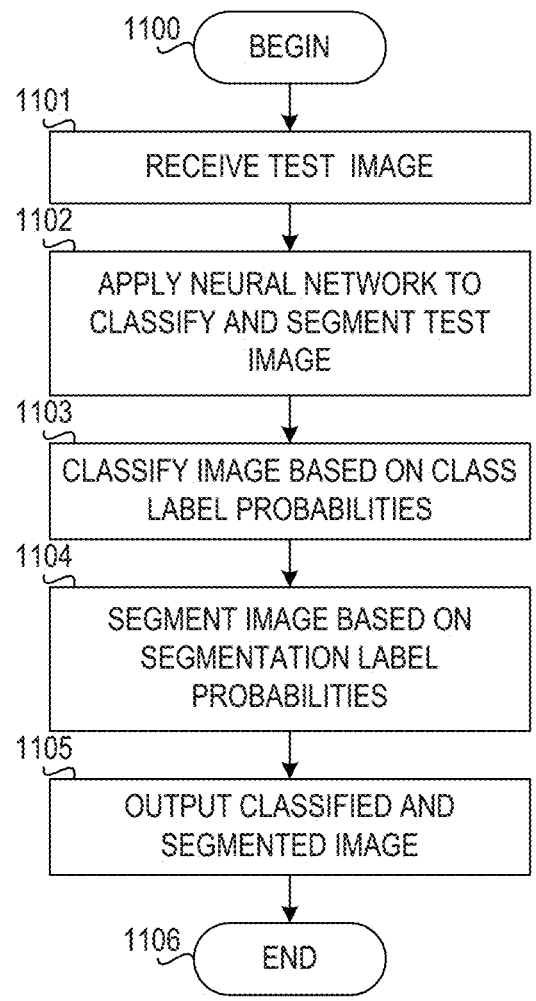
FIG. 11 is a flowchart illustrating operation of a mechanism for using a deep learning neural network to perform anatomical segmentation identifying modes and viewpoints in biomedical images in accordance with an illustrative embodiment.

FIG. 11 is a flowchart illustrating operation of a mechanism for using a deep learning neural network to perform anatomical segmentation identifying modes and viewpoints in biomedical images in accordance with an illustrative embodiment. Operation begins (block 1100), and the mechanism receives a test image (block 1101). A test image may be an unlabeled image for testing the neural network or may be a biomedical image for which a user wants to perform segmentation and classification. The mechanism applies the neural network to the test image to generate a probability for each class label and segmentation label (block 1102).

Then, the mechanism classifies the image based on class label probabilities (block 1103). In one embodiment, the mechanism applies a set of rules to the probabilities for each class label and segmentation labels to determine a most likely combination of modality, viewpoint, and segmentation label(s). The mechanism also segments the image based on the segmentation probabilities (block 1104).

In one embodiment, the neural network generates an image map for each segmentation label. The image map includes for each pixel a probability that the pixel is part of the organ or structure corresponding to the segmentation label. For each pixel an argmax operator is applied to result in the label/organ with highest probability. In one embodiment, a post-processing step is applied to remove segmentations with low confidence and/or structures that conflict with rules in 907 in FIG. 9. Thereafter, the mechanism outputs the classified and segmented image (block 1105), and operation ends (block 1106).

The classifier determines if the image is CT, MRI, CXR, US, etc. The viewpoint classifier determines the orientation as coronal, sagittal, axial, 2Ch view, etc. The organ detection detects particular anatomical structures, e.g., lungs, myocardium, liver, etc. The segmentation segments the anatomical structures of interest with any anomalies, such as tumors, masses, etc. The combination of these elements into a single network is achieved by having a two-headed network with two loss functions, one for segmentation and one for classification.

Thus, the illustrative embodiments provide advantages in that a single network is simpler to train than many different networks. There is a shorter inference time at deployment as medical images run through a single model instead of many models, such as in traditional cascade approaches. For traditional cascade approaches, the accuracy is calculated as the multiplication of all the cascade network components in each dissension branch. This requires near perfect accuracies, especially in the earlier stages. On the other hand, with a single network, as in the illustrative embodiments, the accuracy is exactly the network's accuracy.

In addition, because a single network is being used fir a plurality of different modalities, anatomical structure information may be learned and transferred between modalities. That is, segmentation algorithms may be applied across modalities with different data sets. Traditionally, algorithms or networks are focused on solving a particular problem in one modality. The network of the illustrative embodiments is more extensible and does not require construction of any decision trees, as opposed to traditional approaches.

Because the proposed deep network architecture is a single network, it occupies less memory and resources by using a fraction of parameters compared to multiple single modality networks. In addition, the proposed deep network architecture avoids error propagation compared to the traditional approach.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a multi-modal classification and segmentation engine for anatomical segmentation identifying modes and viewpoints in biomedical images, the method comprising:

training a single neural network to perform simultaneous classification and segmentation using a set of training images, wherein the neural network comprises a classification head and a segmentation head, wherein the classification head generates a plurality of class label probabilities for a plurality of class labels, and wherein the segmentation head generates a plurality of segmentation label probabilities for a plurality of segmentation labels;
providing, by the multi-modal classification and segmentation engine, a biomedical image as the input image to the neural network;
outputting, by the neural network, the plurality of class label probabilities and the plurality of segmentation label probabilities based on the input image;
classifying, by a post-processing component executing within the multi-modal classification and segmentation engine, the biomedical image as an identified modality and an identified viewpoint based on the plurality of class label probabilities;
segmenting, by the multi-modal classification and segmentation engine, the biomedical image based on the plurality of segmentation label probabilities; and
outputting, by the multi-modal classification and segmentation engine, the classified and segmented biomedical image.

2. The method of claim 1, wherein the set of training images comprise a plurality of biomedical images covering a plurality of modalities, viewpoints, and segmentations.

3. The method of claim 1, wherein the neural network comprises a convolutional neural network.

4. The method of claim 3, wherein the convolutional neural network comprises a U-net with multiple heads.

5. The method of claim 4, wherein the convolutional neural network comprises a concatenating path and an expanding path, wherein the convolutional neural network comprises the classification head at the end of the concatenating path and the segmentation head at the end of the expanding path.

6. The method of claim 1, wherein the plurality of class labels comprises class labels for a plurality of modalities.

7. The method of claim 6, wherein the plurality of modalities comprise X-ray, magnetic resonance imaging (MRI), computerized tomography (CT), and ultrasound.

8. The method of claim 7, wherein the plurality of class labels comprise chest X-ray (CXR), short axis MRI (SAX), two-channel MRI (2Ch), four-channel MRI (4Ch), CT, brightness modulation ultrasound (Bmod), and Doppler ultrasound (Dop).

9. The method of claim 1, wherein the plurality of segmentation labels comprise lung, heart, myocardium, left ventricle, right ventricle, left atrium, right atrium, and Doppler waveform.

10. The method of claim 1, wherein the neural network generates an image map for each segmentation label, wherein the image map comprises for each pixel a probability that the pixel is part of an organ or structure corresponding to the segmentation, wherein segmenting the biomedical image comprises comparing each probability to a threshold.

11. A computer program product comprising a non-transitory computer readable medium having a computer readable program stored therein, wherein the computer readable program, when executed on a computing device, causes the computing device to implement a multi-modal classification and segmentation engine for anatomical segmentation identifying modes and viewpoints in biomedical images, wherein the computer readable program causes the computing device to:
train a single neural network to perform simultaneous classification and segmentation using a set of training images, wherein the neural network comprises a classification head and a segmentation head, wherein the classification head generates a plurality of class label probabilities for a plurality of class labels, and wherein the segmentation head generates a plurality of segmentation label probabilities for a plurality of segmentation labels;
provide, by the multi-modal classification and segmentation engine, a biomedical image as the input image to the neural network;
output, by the neural network, the plurality of class label probabilities and the plurality of segmentation label probabilities based on the input image;
classify, by a post-processing component executing within the multi-modal classification and segmentation engine, the biomedical image as an identified modality and an identified viewpoint based on the plurality of class label probabilities;
segment, by the multi-modal classification and segmentation engine, the biomedical image based on the plurality of segmentation label probabilities; and
output, by the multi-modal classification and segmentation engine, the classified and segmented biomedical image.

12. The computer program product of claim 11, wherein the set of training images comprise a plurality of biomedical images covering a plurality of modalities, viewpoints, and segmentations.

13. The computer program product of claim 11, wherein the neural network comprises a convolutional neural network.

14. The computer program product of claim 13, wherein the convolutional neural network comprises a U-net with multiple heads.

15. The computer program product of claim 14, wherein the convolutional neural network comprises a concatenating path and an expanding path, wherein the convolutional neural network comprises the classification head at the end of the concatenating path and the segmentation head at the end of the expanding path.

16. The computer program product of claim 11, wherein the plurality of class labels comprises class labels for a plurality of modalities.

17. The computer program product of claim 16, wherein the plurality of modalities comprises X-ray, magnetic resonance imaging (MRI), computerized tomography (CT), and ultrasound.

18. The computer program product of claim 17, wherein the plurality of class labels comprise chest X-ray (CXR), short axis MRI (SAX), two-channel MRI (2Ch), four-channel MRI (4Ch), CT, brightness modulation ultrasound (Bmod), and Doppler ultrasound (Dop).

19. The computer program product of claim 11, wherein the plurality of segmentation labels comprise lung, heart, myocardium, left ventricle, right ventricle, left atrium, right atrium, and Doppler waveform.

20. An apparatus, comprising:
a processor; and
a memory coupled to the processor, wherein the memory comprises instructions which, when executed by the processor, cause the processor to implement a multi-modal classification and segmentation engine for anatomical segmentation identifying modes and viewpoints in biomedical images, wherein the instructions cause the processor to:
train a single neural network to perform simultaneous classification and segmentation using a set of training images, wherein the neural network comprises a classification head and a segmentation head, Wherein the classification head generates a plurality of class label probabilities for a plurality of class labels, and wherein the segmentation head generates a plurality of segmentation label probabilities for a plurality of segmentation labels;

provide, by the multi-modal classification and segmentation engine, a biomedical image as the input image to the neural network;

output, by the neural network, the plurality of class label probabilities and the plurality of segmentation label probabilities based on the input image;

classify, by a post-processing component executing within the multi-modal classification and segmentation engine, the biomedical image as an identified modality and an identified viewpoint based on the plurality of class label probabilities;

segment, by the multi-modal classification and segmentation engine, the biomedical image based on the plurality of segmentation label probabilities; and output, by the multi-modal classification and segmentation engine, the classified and segmented biomedical image.

* * * * *